(12) United States Patent
Boyle

(10) Patent No.: US 11,439,346 B2
(45) Date of Patent: Sep. 13, 2022

(54) ROBOTIC DEVICE FOR ASSISTING INDIVIDUALS WITH A MENTAL ILLNESS

(71) Applicant: Jacob T. Boyle, Hillsdale, NJ (US)

(72) Inventor: Jacob T. Boyle, Hillsdale, NJ (US)

( * ) Notice: Subject to any disclaimer, the term of this patent is extended or adjusted under 35 U.S.C. 154(b) by 925 days.

(21) Appl. No.: 16/239,301

(22) Filed: Jan. 3, 2019

(65) Prior Publication Data

US 2020/0214626 A1 Jul. 9, 2020

(51) Int. Cl.

| | |
|---|---|
| *G09B 19/00* | (2006.01) |
| *A61B 5/00* | (2006.01) |
| *A61B 5/16* | (2006.01) |
| *A61B 5/0205* | (2006.01) |
| *A61B 5/01* | (2006.01) |
| *G16H 20/70* | (2018.01) |
| *G06V 40/16* | (2022.01) |
| *A61B 5/08* | (2006.01) |
| *A61B 5/024* | (2006.01) |

(52) U.S. Cl.
CPC .......... *A61B 5/4836* (2013.01); *A61B 5/0002* (2013.01); *A61B 5/0077* (2013.01); *A61B 5/01* (2013.01); *A61B 5/02055* (2013.01); *A61B 5/165* (2013.01); *A61B 5/6896* (2013.01); *A61B 5/7267* (2013.01); *A61B 5/742* (2013.01); *A61B 5/7405* (2013.01); *A61B 5/7455* (2013.01); *G06V 40/174* (2022.01); *G16H 20/70* (2018.01); *A61B 5/024* (2013.01); *A61B 5/0816* (2013.01)

(58) Field of Classification Search
CPC ... A61B 5/4836; A61B 5/0002; A61B 5/0077; A61B 5/01; A61B 5/02055; A61B 5/165; A61B 5/6896; A61B 5/7267; A61B 5/7405; A61B 5/742; A61B 5/7455; A61B 5/024; A61B 5/0816; G16H 20/70; G06V 40/174

USPC ......................................................... 343/236
See application file for complete search history.

(56) References Cited

U.S. PATENT DOCUMENTS

| | | |
|---|---|---|
| 479,567 A | 7/1892 | Maddox |
| 5,544,649 A | 8/1996 | David et al. |
| 6,175,772 B1 | 1/2001 | Kamiya et al. |
| 6,581,048 B1 | 6/2003 | Werbos |
| 6,629,242 B2 | 9/2003 | Kamiya et al. |
| 6,684,127 B2 * | 1/2004 | Fujita ..................... G06N 3/008 446/268 |
| 7,515,992 B2 | 4/2009 | Sawada et al. |
| 7,720,572 B2 | 5/2010 | Ziegler et al. |
| 7,813,836 B2 | 10/2010 | Wang et al. |
| 7,835,926 B1 | 11/2010 | Naidoo et al. |
| 7,853,375 B2 | 12/2010 | Tuff |
| 7,912,733 B2 | 3/2011 | Clements et al. |
| 8,226,417 B2 | 7/2012 | Mitsuyoshi |
| 8,527,213 B2 | 9/2013 | Kailas et al. |

(Continued)

*Primary Examiner* — Zhen Y Wu

(74) *Attorney, Agent, or Firm* — Ellenoff Grossman & Schole LLP; James M. Smedley; Alex Korona

(57) ABSTRACT

A robot is devoted to assisting users with mental illness with software and hardware to provide multiple user modules, including psychotherapy, sympathy, meditation training, expression gestures and words, and hugging responses. Biofeedback and medical data collection are also achieved. Cameras, microphones, speakers, sensors and artificial intelligence, including speech recognition, voice identification and other algorithms are employed. At least three levels of security, and preferably four are used: user, caregiver, manager and programmer personnel are provided different levels of access.

19 Claims, 10 Drawing Sheets

(56) References Cited

U.S. PATENT DOCUMENTS

| | | | |
|---|---|---|---|
| 8,751,042 B2 * | 6/2014 | Lee | G06N 5/02 |
| | | | 700/264 |
| 8,909,370 B2 | 12/2014 | Stiehl et al. | |
| 9,378,065 B2 | 6/2016 | Shear et al. | |
| 9,679,495 B2 | 6/2017 | Cohen | |
| 9,792,160 B2 | 10/2017 | Shear et al. | |
| 9,796,095 B1 | 10/2017 | Hanson et al. | |
| 9,802,314 B2 | 10/2017 | Yamane et al. | |
| 9,805,381 B2 | 10/2017 | Frank et al. | |
| 9,904,579 B2 | 2/2018 | Shear et al. | |
| 9,955,902 B2 | 5/2018 | Frank et al. | |
| 10,075,384 B2 | 9/2018 | Shear et al. | |
| 2002/0103576 A1 | 8/2002 | Takamura et al. | |
| 2003/0182123 A1 | 9/2003 | Mitsuyoshi | |
| 2005/0154265 A1 * | 7/2005 | Miro | G07C 9/37 |
| | | | 704/E15.045 |
| 2005/0197739 A1 | 9/2005 | Nada et al. | |
| 2006/0179022 A1 | 8/2006 | Holland | |
| 2007/0192910 A1 * | 8/2007 | Vu | B25J 19/06 |
| | | | 901/17 |
| 2009/0055019 A1 * | 2/2009 | Stiehl | B25J 9/1671 |
| | | | 901/17 |
| 2012/0295510 A1 * | 11/2012 | Boeckle | G09B 5/06 |
| | | | 446/72 |
| 2013/0078600 A1 * | 3/2013 | Fischer | G09B 19/00 |
| | | | 434/236 |
| 2014/0221797 A1 * | 8/2014 | Bailey | A61B 5/0205 |
| | | | 600/595 |
| 2015/0273697 A1 * | 10/2015 | Abdullah | B25J 11/009 |
| | | | 901/1 |
| 2016/0140320 A1 * | 5/2016 | Moturu | G16H 20/70 |
| | | | 434/236 |
| 2016/0358276 A1 * | 12/2016 | Stephenson | G16H 20/00 |
| 2018/0176727 A1 | 6/2018 | Williams | |
| 2018/0261332 A1 | 9/2018 | Baeuerle | |
| 2018/0272190 A1 | 9/2018 | Miura et al. | |
| 2019/0054627 A1 * | 2/2019 | Gomes | B25J 9/0021 |
| 2019/0366558 A1 * | 12/2019 | Gupta | B25J 11/0005 |
| 2020/0114521 A1 * | 4/2020 | Mahoor | G06V 40/174 |
| 2020/0324411 A1 * | 10/2020 | Li | B25J 9/126 |
| 2021/0387346 A1 * | 12/2021 | Gillett | B25J 19/0075 |

* cited by examiner

CONTINUED FROM FIGURE 1A

ARTIFICIAL INTELLIGENCE, SOFTWARE, HARDWARE, WITH CORRESPONDING CONNECTIONS AND LOCATIONS ON TORSO/HEAD/OPTIONAL APPENDAGE(S)

(i) FIRST USER IMPACT MODULE – COMPANIONSHIP (TWO WAY COMMUNICATOIN)
(ii) SECOND USER IMPACT MODULE – GUIDED MEDITATION
(iii) THIRD USER IMPACT MODULE – PSYCHOTHERAPY
(iv) FOURTH USER IMPACT MODULE – BIOFEEDBACK
(v) FIFTH USER IMPACT MODULE – EMERGENCY HIGH RISK ALERT
(vi) PRESSURE SENSOR FEEDBACK SOFTWARE (FOR RECOGNIZING AND ACKNOWLEDGING HUGS)
(vii) CAMERA – RECEIVING/PROCESSING SOFTWARE
(viii) EMOTIONAL EXPRESSIONS SOFTWARE

ROBOTIC DEVICE FOR ASSISTING INDIVIDUALS WITH A MENTAL ILLNESS

REFERENCE TO RELATED APPLICATION(S)

The present application is related to and priority is hereby claimed and is a continuation in part of United States of America. Provisional Patent Application, as follows: Provisional Application No. 62/662,692, titled "MARCO—THE MENTALLY ASSISTIVE ROBOTIC COMPANION", filed on Apr. 25, 2018 by the same inventors herein.

BACKGROUND OF INVENTION a. Field of Invention

The present invention generally relates to the implementation of Artificial Intelligence (AI) and robotics for the treatment of bipolar disorder, depression, and general anxiety disorder (GAD). In particular, it relates to the development of an artificially intelligent robotic companion for the assistance of individuals with the aforementioned mental illnesses in a home, clinical or other setting. Specifically, it relates to the assistance of both individuals with mental illness and their caregivers to provide treatment for the patient and monitoring and accurate diagnosis for the use of the caregiver. Thus, the present invention is a unique robotic device that utilizes artificial intelligence, microphones (artificial listening), speech recognition, speakers (artificial talk, exchange, instruction), monitoring, facial expression recognition and response, training and treatment features to provide instantaneous companionship to a user (with mental illness), as well as instructional, behavioral and other feedback and training, as well as other aspects of treatments and aids towards assistance in reducing or alleviating psychological problems. These present invention robots include biofeedback, data storage, diagnosis, medical metrics, hugging sensors, hugging responses, relaxation-meditation training and exercises, and behavioral psychology sessions.

b. Description of Related Art

The following patents are representative of the field pertaining to the present invention:

U.S. Design Pat. No. 479,567 S1, titled Seal Robot, describes an ornamental design of a seal robot.

U.S. Pat. No. 5,544,649, titled Ambulatory Patient Health Monitoring Techniques Utilizing Interactive Visual Communication, describes an ambulatory (in the home) patient health monitoring system, wherein the patient is monitored by a health care worker at a central station, while the patient is at a remote location. The patient may be a person having a specific medical condition monitored or may be an elderly person desiring general medical surveillance in the home environment. Cameras are provided at the patient's remote location and at the central station such that the patient and the health care worker are in interactive visual and audio communication. A communications network such as an interactive cable television is used for this purpose. Various medical condition sensing and monitoring equipment are placed in the patient's home, depending on the particular medical needs of the patient. The patient's medical condition is measured or sensed in the home and the resulting data is transmitted to the central station for analysis and display. The health care worker then is placed into interactive visual communication with the patient concerning the patient's general well-being, as well as the patient's medical condition. Thus, the health care worker can make "home visits" electronically, twenty-four hours a day.

U.S. Pat. No. 6,175,772, titled User Adaptive Control Of Object Having Pseudo-Emotions By Learning Adjustments Of Emotion Generating And Behavior Generating Algorithms, describes a control method for controlling operation of an object used by a user in an environment that includes the steps of: defining pseudo-emotions of the object for deciding output of the object, in relation to the user's state; formulating emotion generation algorithms to establish the relationship between the user's state and the pseudo-emotions; formulating behavior decision algorithms to establish the relationship between input, including the pseudo-emotions, and the behavior of the object; detecting the user's state; generating a pseudo-emotion of the object based on the user's state using the emotion generation algorithms; making the object behave based on the user's state and the pseudo-emotion using the behavior decision algorithms; evaluating reaction of the user in response to the behavior of the object; and if the reaction of the user does not match the pseudo-emotion of the object in the emotion generation algorithms, adjusting at least either of the emotion generation algorithms or the behavior decision algorithms, followed by learning the adjustment. The object can detect the user's state in a visual, tactile, and auditory manner as do humans, and can act upon generation of pseudo-emotions based thereon. Thus, natural communication between the user and the object can be performed, i.e., more human like communication can be established. A control method for controlling operation of an object used by a user in an environment includes the steps of: defining pseudo-emotions of the object for deciding output of the object, in relation to the user's state; formulating emotion generation algorithms to establish the relationship between the user's state and the pseudo-emotions; formulating behavior decision algorithms to establish the relationship between input, including the pseudo-emotions, and the behavior of the object; detecting the user's state; generating a pseudo-emotion of the object based on the user's state using the emotion generation algorithms; making the object behave based on the user's state and the pseudo-emotion using the behavior decision algorithms; evaluating reaction of the user in response to the behavior of the object; and if the reaction of the user does not match the pseudo-emotion of the object in the emotion generation algorithms, adjusting at least either of the emotion generation algorithms or the behavior decision algorithms, followed by learning the adjustment. The object can detect the user's state in a visual, tactile, and auditory manner as do humans, and can act upon generation of pseudo-emotions based thereon. Thus, natural communication between the user and the object can be performed, i.e., more human like communication can be established.

U.S. Pat. No. 6,581,048, titled 3-Brain Architecture For An Intelligent Decision And Control System describes a method and system for intelligent control of external devices using a mammalian brain-like structure having three parts. The method and system include a computer-implemented neural network system which is an extension of the model-based adaptive critic design and is applicable to real-time control (e.g., robotic control) and real-time distributed control. Additional uses include data visualization, data mining, and other tasks requiring complex analysis of inter-relationships between data.

U.S. Pat. No. 6,629,242, titled Environment Adaptive Control Of Pseudo-Emotion Generating Machine By Repeatedly Updating And Adjusting At Least Either Of Emotion Generation And Behavior Decision Algorithms, describes a control method for controlling operation of an object used by a user in an environment includes the steps of: defining pseudo-emotions of the object for deciding output of the object, in relation to the user's state; formulating emotion generation algorithms to establish the relationship between the user's state and the pseudo-emotions; formulating behavior decision algorithms to establish the relationship between input, including the pseudo-emotions, and the behavior of the object; detecting the user's state; generating a pseudo-emotion of the object based on the user's state using the emotion generation algorithms; making the object behave based on the user's state and the pseudo-emotion using the behavior decision algorithms; evaluating reaction of the user in response to the behavior of the object; and if the reaction of the user does not match the pseudo-emotion of the object in the emotion generation algorithms, adjusting at least either of the emotion generation algorithms or the behavior decision algorithms, followed by learning the adjustment. The object can detect the user's state in a visual, tactile, and auditory manner as do humans, and can act upon generation of pseudo-emotions based thereon. Thus, natural communication between the user and the object can be performed, i.e., more human like communication can be established.

U.S. Pat. No. 6,684,127, titled Method Of Controlling Behaviors Of Pet Robots, describes a robotic system, robot apparatus, and a control method wherein behaviors suitable for a robot are embodied based on information distributed by a number of information distributing devices. Also, the robotic system, robot apparatus, and a control method are designed based on information distributed by the number of information distributing devices such that a robot is prohibited from embodying corresponding behaviors out of the behaviors the robot could embody, or that prohibition on the robot embodying corresponding behaviors is withdrawn. Furthermore, control data for the robot to generate behaviors can be modified to meet the desires of the robot and/or the user of the robot.

U.S. Pat. No. 7,515,992, titled Robot Apparatus And Emotion Representing Method Therefor, describes a robot apparatus with the storage capacity necessary for holding motion data which is diminished in representing the emotion by motions exploiting the body resources. In demonstrating component behaviors of the robot apparatus, the basic posture, as the posture at the start time of one or plural movements forming a component behavior, is changed to express the emotion. Specifically, the robot apparatus includes variations for expressing the emotion for the basic posture (basic posture for the emotion). The respective resources are actuated from the basic posture for the emotion and reversion is made again to the basic posture to demonstrate the emotion. At this time, the robot apparatus 1 holds data, such as joint angles, in the course of the movements.

U.S. Pat. No. 7,720,572, titled Companion Robot For Personal Interaction, describes a robot system that includes a base station and a robot. The base station includes a wireless transceiver configured to communicate TCP/IP transmissions over a local wireless protocol, a wired Ethernet connector for communicating TCP/IP transmissions over a local wired Ethernet accessing the Internet, and an access point circuit for transferring TCP/IP transmissions between the local wired Ethernet and local wireless protocol. The access point circuit is limited to a predetermined IP address locked to the robot, a predetermined shell level encryption locked to the robot, and predetermined ports to the Internet open only to the robot. The robot includes a wireless transceiver configured to communicate TCP/IP transmissions over a local wireless protocol and a client circuit for transferring TCP/IP transmissions over the local wireless protocol.

U.S. Pat. No. 7,813,836, titled Protocol For A Remotely Controlled Videoconferencing Robot, describes a robotic system that includes a robot and a remote station. The remote station can generate control commands that are transmitted to the robot through a broadband network. The control commands can be interpreted by the robot to induce action such as robot movement or focusing a robot camera. The robot can generate reporting commands that are transmitted to the remote station through the broadband network. The reporting commands can provide positional feedback or system reports on the robot.

U.S. Pat. No. 7,835,926, titled Method For Conducting A Home Health Session Using An Integrated Television-Based Broadband Home Health System, describes an integrated home health system includes a television-based patient station, a first provider station for providing telemedicine or other healthcare services to a patient located at the patient station, a second provider station for providing caregiver services to the patient, a third provider station for providing emergency response services to the patient and a system management station coupled together by a data network. In addition to various management operations performed on behalf of the integrated home health system, the system management station is further configured to provide various home health services to the patient located at the patient station, either alone, or in conjunction with one or more of the first, second and/or third provider stations.

U.S. Pat. No. 7,853,357, titled Robot Device, Behavior Control Method Thereof, And Program, describes a robot device with an action selecting/control system includes a plurality of elementary action modules each of which outputs an action when selected, an activation level calculation unit to calculate an activation level AL of each elementary action on the basis of information from an internal-state manager and external-stimulus recognition unit and with reference to a data base, and an action selector to select an elementary action whose activation level AL is highest as an action to be implemented. Each action is associated with a predetermined internal state and external stimulus. The activation level calculation unit calculates an activation level AL of each action on the basis of a predicted satisfaction level variation based on the level of an instinct for an action corresponding to an input internal state and a predicted internal-state variation predictable based on an input external stimulus.

U.S. Pat. No. 7,912,733, titled System, Method And Program Product For Delivering Medical Services From A Remote Location, describes a system, program product, and methods related to enhanced medical services delivery to geographically distributed patient populations by remotely located physicians are provided. An embodiment of the system includes a remote medical services server, a plurality of patient electronic medical records stored in the memory of the remote medical services server, and a remote medical services program product stored in the memory of the remote medical services server adapted to access the plurality of patient electronic medical records to thereby allow display of and data entry in a selected patient electronic medical record. A patient medical service delivery station captures patient video images and displays remote physician video images. A remote physician medical service delivery suite in communication with the patient medical service delivery station through the communications network captures remote physician video images and displays patient video images and patient electronic medical records, to allow the remote physician to perform remote patient medical service delivery.

U.S. Pat. No. 8,226,417, titled Will Expression Model Device, Psychological Effect Program, And Will Expression Simulation Method, provides a will-expression modeling device simulating human will-expression responding to an direction input given from the outside, which includes an interest interpretation section, an emotion creating section and a will-expression section. The interest interpretation section collates the direction input with a predetermined hedonic interest relationship table and outputs a mood factor representing pleasure, displeasure or the like. The emotion creating section prepares a plurality of emotional states obtained by modeling human emotions as data and causes state transitions to occur in the emotional states according to the mood factor to simulate a change in human emotion responding to the direction input. The will-expression section prepares in advance a plurality of mental-will states obtained by modeling human will as data and selects a new mental-will state from the emotional states or a "combination of a mental-will state and an emotional state".

U.S. Pat. No. 8,527,213, titled Monitoring Wellness Using A Wireless Handheld Device, describes a method for detecting a subject's stress level associated with an activity that includes (a) connecting the subject to a sensor that senses a value of a biometric; (b) during the activity, (i) repeatedly sensing the value of the biometric over each of a plurality of time windows; and (ii) computing, for each time window, a deviation in the sensed values of the biometric; and (c) detecting the stress level based on the computed deviations. In one implementation, the value of the biometric is a skin temperature measurement. The method may be implemented as an application in a wireless handheld device, such as a cellular telephone.

U.S. Pat. No. 8,909,370 A1 (Application Publication no. 2009/0055019 A1), titled Interactive Systems Employing Robotic Companions, describes an interactive system for interacting with a sentient being. The system includes a robotic companion of which the sentient being may be a user and an entity which employs the robot as a participant in an activity involving the user. The robotic companion responds to inputs from an environment that includes the user during the activity. The robotic companion is capable of social and affective behavior either under control of the entity or in response to the environment. The entity may provide an interface by which an operator may control the robotic companion. Example applications for the interactive system include as a system for communicating with patients that have difficulties communicating verbally, a system for teaching remotely-located students or students with communication difficulties, a system for facilitating social interaction between a remotely-located relative and a child, and systems in which the user and the robot interact with an entity such as a smart book. Also disclosed are control interfaces for the robotic companion, techniques for rendering the robotic companion sensitive to touch and responding to those touches, and techniques for providing quiet, backdrivable motion to components of the robotic companion.

U.S. Pat. No. 9,679,495, titled Systems And Methods For Computerized Interactive Training describes interactive electronic training systems and methods. Certain embodiments provide preprogrammed video, audio, and/or textual presentations of training materials which provide information related to skills/information to be trained. A scenario including real or animated actors is presented, simulating an interaction. The training system presents related queries for the trainee who audibly responds. The training system stores a score based in part on a comparison of the trainee's response with an answer stored in training system memory. Optionally, the scores are substantially immediately presented by the system to the trainee.

U.S. Pat. No. 9,796,095, titled System And Method For Controlling Intelligent Animated Characters, describes a system and method for controlling animated characters. The system involves an animated character mapping perception into a number of domains, including a world domain, linguistic domain and social domain. The system is computationally perceived items that should be abstracted from the character's environment for processing. The animated character is able to utilize different levels of information gathering or learning, different levels of decision making, and different levels of dynamic responses to provide life-like interactions.

U.S. Pat. No. 9,802,314, titled Soft Body Robot For Physical Interaction With Humans, describes a robot designed for reducing collision impacts during human interaction. The robot includes a robot controller including a joint control module. The robot includes a link including a rigid support element and a soft body segment coupled to the rigid support element, and the body segment includes a deformable outer sidewall enclosing an interior space. The robot includes a pressure sensor sensing pressure in the interior space of the link. A joint is coupled to the rigid support element to rotate or position the link. During operations, the robot controller operates the joint based on the pressure sensed by the pressure sensor. The robot controller modifies operation of the joint from a first operating state with a servo moving or positioning the joint to a second operating state with the servo operating to allow the joint to be moved or positioned in response to outside forces applied to the link.

U.S. Pat. No. 9,805,381, titled Crowd-Based Scores For Food From Measurements Of Affective Response, disclose computation of a preference score for a certain type of food. In some embodiments described herein, measurements of affective response of at least ten users are collected. The measurements may include various values indicative of physiological signals and/or behavioral cues of the at least ten users. Each measurement of a user is taken with a sensor coupled to the user up to four hours after the user consumed the certain type of food. A preference score is computed based on the measurements. The preference score is indicative of how much the at least ten users enjoyed consuming the certain type of food and/or how well they felt after consuming the certain type of food.

U.S. Pat. No. 9,955,902, titled Notifying A User About A Cause Of Emotional Imbalance, disclosure include systems, methods, and/or computer programs that may be used to notify a user about a cause of emotional imbalance. Some embodiments described herein involve determining when a user is in a state of emotional imbalance based on a measurement of affective response of the user, which is taken with a sensor. Factors characterizing an event to which the measurement corresponds are examined in order to select a certain factor that, based on a model of the user, has an effect on the user that is congruous with the measurement of affective response. The user is notified about the certain factor in order to make the user more aware of the certain factor and its effect on the user.

The following four patents have the same inventors and similar or the same titles/abstracts. They are related patents and do include the idea of treatment of mental illness as one of its aspects the inventions:

U.S. Pat. No. 9,378,065, titled Purposeful Computing; U.S. Pat. No. 9,792,160, titled Methods And Systems Supporting A Resource Environment For Contextual Purpose Computing; U.S. Pat. No. 9,904,579, titled Methods And Systems For Purposeful Computing; U.S. Pat. No. 10,075,384, titled Purposeful Computing, all describe a system, method, and computer-readable storage medium configured to facilitate user purpose in a computing architecture. Mental illness treatments are contemplated within their formats.

Notwithstanding the prior art, the present invention is neither taught nor rendered obvious thereby.

SUMMARY OF INVENTION

The present invention is directed to a robotic device for assisting users with a mental illness, especially those in need of psychotherapy and other treatments and interactions. Thus, the present invention robotic device includes: (a) a robotic support frame having sufficient structure to support the subsequently described components, and having a main torso and a head; (b) a central processing unit within the robotic support frame, the central processing unit including software to operate at least five user impact modules and including artificial intelligence software, voice recognition software, speech output software, and a graphical user interface connected to an external screen; (c) a power supply component selected from the group consisting of internal power supply and external power connection, connected to the central processing unit; (d) the external screen attached to the robotic support frame and having visual display output and having at least touch screen input; (e) at least one camera attached to the robotic support frame for viewing a user and connected to the central processing unit; (f) at least one microphone attached to the robotic support frame for receiving audio input and connected to the central processing unit; (g) at least one speaker attached to the robotic support frame for transmitting audio output and connected to the central processing unit; (h) hardware and additional software functionally connected to the central processing unit and to the artificial intelligence software, to the voice recognition software, and to the speech output software, including at least five user impact modules; and (i) an exoskin attached to at least a portion of the robotic support frame, the exoskin having a plurality of sensors for sensing inward pressure, the plurality of sensors being connected to the pressure sensing-responding software of the central processing unit.

The additional present invention robotic device hardware and software mentioned above includes: (i) a first user impact module, being a companion module, with two-way communications to establish companionship with a user; (ii) a second user impact module, being a guided meditation module, to provide assistance to a user in conducting personal meditation; (iii) a third user impact module, being a psychotherapy treatment module, to receive input from a user, recognize symptoms of a mental illness, define a treatment regimen, and provide corrective guidance and treatment to a user; (iv) a fourth user impact module, being a biofeedback module to receive user bio-information and to record and direct biofeedback data; (v) a fifth user impact module, being an emergency high risk alert system to receive and recognize suicidal tendencies and to report it as an emergency to a third party monitor; (vi) a pressure sensing-responding software connected to exoskin sensors and providing positive feedback to a user in response to sensing of inward pressure; (vii) camera receiving software with emotional identification features; (viii) emotional expressions software to provide a user with selected emotional responses via at least one emotional expression mechanism selected from the group consisting of movement of the head, movement of a component of the head, light changes, audio outputs, and artificial intelligence speech outputs, as well as other software and hardware consistent with the foregoing.

In some embodiments of the present invention robotic device for assisting users with a mental illness, various additions, refinements and functionalities may include: the guided meditation module includes pre-meditation training sessions and actual meditation sessions guiding a user through meditation; the mental illness treatment module includes diagnosis analysis with appropriate questions to a user and storage and analysis of responses from a user, and subsequent instructional sessions providing a user with alternative reactions to negative emotion situations; the mental illness treatment module includes use of recognized behavioral therapy; the recognized behavior therapy is preferably cognitive behavioral therapy.

In some embodiments of the present invention robotic device for assisting users with a mental illness, the exoskin is attached to the torso to enable a user hugging feature that initiates a positive response from the robotic device. By "exoskin" is meant an artificial skin comprising at least on layer of soft material mounted on the outside of at least a portion of the robot support frame. This exoskin may be a single layer, a plurality of layers, or an integral skin layer (such as integral skin urethane foam). It may be made of foam or memory foam, with another top layer, such as clothing, rubberized cloth, faux fur, etc. or it may be a composite of multiple layers.

In some embodiments of the present invention robotic device for assisting users with a mental illness, the artificial intelligence software includes visual emotion recognition that studies a user's facial expression, identifies facial landmarks, compares the facial landmarks to training data, determines the user's emotional state and responds with a defined response to the emotional state. In some embodiments, the software includes facial movement tracking and hardware connected to the camera to move the camera in response to positional movement of the facial landmarks of the user.

In some embodiments of the present invention robotic device for assisting users with a mental illness, there is a communications module for external connectivity that includes at least one communications unit selected from the group consisting of a connectivity port and wireless transmitter-receiver and WIFI connectivity.

In some embodiments of the present invention robotic device for assisting users with a mental illness, the robotic device further includes at an appendage with a human physical data sensing mechanism with user contact sensing of at least one parameter selected from the group consisting of pulse, temperature, and aspiration rate.

In some embodiments of the present invention robotic device for assisting users with a mental illness, the robotic device further includes at least three distinct levels of entry security for access to the central processing unit, including: a first level of security, being a user's level of security, permitting a user to be recognized and to be limited in the use of the robotic device only for user designated purposes and to exclude a user from altering, transferring and eliminating data, from entering a higher level of security, thereby being prevented from operating at those levels of security; a second level of security, being a caretaker level of security, and being a higher level of security than the first level of security, and permitting access to the first level of security, and permitting access to user data for review and report functions, permitting user programming for interaction with various portions of each of the at least five user impact modules; a third level of security, being a manager level of security, and being a higher level of security than the first level of security and the second level of security, and permitting access to the first level of security and the second level of security, and at least permitting access to software for modification and for replacement, for reviewing interaction between a user and a caretaker, and for modifying a treatment for a user. In some of these embodiments, there is a fourth level of security, being a manufacturer's level of security, and permitting access to the first level of security, the second level of security, and the third level of security and permitting hardware and software modifications, replacements and bypasses.

In some embodiments of the present invention robotic device for assisting users with a mental illness, the mental illness treatment module includes diagnosis analysis with appropriate questions to a user and storage and analysis of responses from a user, and subsequent instructional sessions providing a user with alternative reactions to negative emotion situations, and, in some preferred embodiments, the mental illness treatment module includes use of recognized behavioral therapy. In some preferred embodiments, the recognized behavior therapy is cognitive behavioral therapy.

In some embodiments of the present invention robotic device for assisting users with a mental illness, the exoskin is attached to the torso to enable a user hugging feature that initiates a positive response from the robotic device.

In some embodiments of the present invention robotic device for assisting users with a mental illness, the artificial intelligence software includes visual emotion recognition that studies a user's facial expression, identifies facial landmarks, compares the facial landmarks to training data, determines the user's emotional state and responds with a defined response to the emotional state. In some embodiments, the software includes facial movement tracking and hardware connected to the camera to move the camera in response to positional movement of the facial landmarks of the user.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE SEVERAL VIEWS OF THE DRAWINGS(S)

The accompanying drawings, which are included to provide a further understanding of the invention and are incorporated in and constitute a part of this specification, illustrate preferred embodiments of the invention and together with the detailed description serve to explain the principles of the invention. In the drawings.

DETAILED DESCRIPTION OF THE EMBODIMENTS

The present invention devices and systems are more fully understood by the following examples in conjunction with this detailed description of the drawings. The present invention has been developed for many purposes and especially for assisting people who have psychological issues and require companionship, guidance, training and privacy. The present invention user friendly robots further offer medical/physical/mental condition monitoring and have high risk alert warnings to third parties. The terms "robotic device" and "robot" are used interchangeably and are intended to mean the present invention devices. The term "module" as used herein in used as a convenience to define various features that have distinct functions, and any module could be a separate software package integrated with the present invention or it could be merely one or more functional features of a program that encompasses two or more or all modules into a single program. Likewise, "artificial intelligence" and "AI" are used to mean the evolving use of AI programs that use inputted (acquired) data coupled with starting data to learn and adapt to create more knowledge over time and to adjust conclusions and responses as more knowledge is evolved. AI programs, speech recognition, artificial speech and facial landmark recognition and the like are within the skill of the artisan, and thus, the details of program codes and program architecture is not included herein.

Figure 1A:
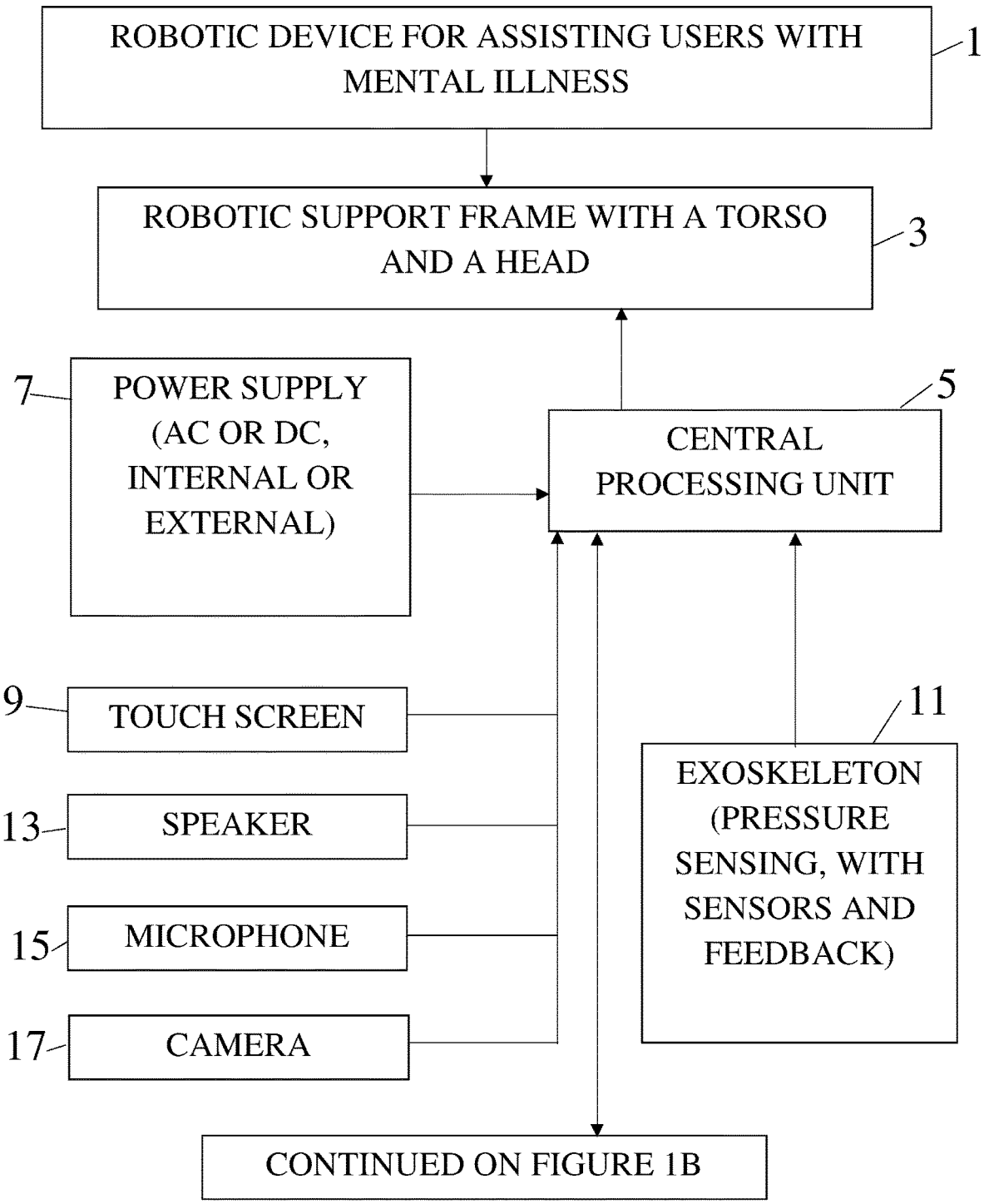
FIG. 1A shows a block diagram of various aspects of a present invention robotic device, continued in FIG. 1B.

FIG. 1A shows a block diagram of various features of the present invention robotic device for assisting users with mental illness, frame 1. The robot has a support frame with a torso and head, frame 2. This support frame may be simple or complex with articulated components for motion. The support frame may be constructed of metal, plastic, composites, carbon fibers or other functional materials and must be constructed to support the various components and connections described below. The torso and head may be ones commonly recognized or uniquely created. For example, the torso could be human, an alien being, an animal, or a fictitious person or animal or creature. It could be of a famous cartoon character, such as Mickey Mouse or Cookie Monster, or a teddy bear, polar bear, or more adult figure, like a friendly human. It may have human features on the head, such as eyes ears, nose, mouth and even further details, such as eyebrows and dimples. The torso may have at least one appendage, but two or four would be preferred in some embodiments. There is a Central Processing Unit ("CPU"), frame 5, which should be taken to be broadly encompassing any type of computer or processor to control and operate the robot in its many functions, movements and software and functional modules described below. The CPU may be fully encompassed within the robotic device or it may be partially separated, such as by wireless connection to a cloud or host server to perform some or many of the robot's tasks. The CPU is powered by a power supply, frame 7, that may be AC or DC, such as battery, solar, fuel cell, or otherwise powered, or a plug-in (wire and external plug) for plugging into outlet power. Preferred is an AC plug for home, office, clinic or other plug-in, coupled with a battery system, much like a laptop. The robot also has mounted thereon, or connected thereto, as well as connected to the CPU, at least one touch screen, frame 9, speaker, frame 11, microphone, frame 15 and camera, frame 17. It is usual for the present invention to have a single touch screen that may or may not include voice recognition/activation; and one or two microphones and speakers and one or more cameras. The support frame of the robot maybe externally, human-like or otherwise and may be dressed or not. At least a portion of the support frame is covered with an exoskin, a type of exoskeleton that is soft and can be squeezed. This exoskeleton, frame 11 of FIG. 1A has pressure sensors to sense and respond to hugging (squeezing). The details continue on FIG. 1B.

FIG. 1b shows a block diagram of various aspects hardware, software and component features of the present invention robotic device. Reference is made to frame 19, wherein the following features are described. The additional present invention robotic device hardware and software mentioned above includes (i) a first user impact module, being a companion module, with two-way communications to establish companionship with a user. This two-way communication in its basic form involves the microphone to capture the speech of the user, the speaker to speak back to the user, either as an initial prompt or discussion beginning, or in response to the user speaking. These robotic inputs and outputs are received, analyzed, understood and preferably stored, and an appropriate reply is formulated and then spoken by the robot. Existing artificial intelligence software is used in conjunction with voice recognition and assimilation software, as well as artificial speech software. Also, there is (ii) a second user impact module, being a guided meditation module, to provide assistance to a user in conducting personal meditation. This is an integral part of the treatment, as meditation is used both as a regular discipline for routine meditation, and as a teaching tool to train the user to drop back in stressful, conflicting or other compromising psychological moments or events. Thus, the meditation contributes to the user being able to embrace a "quieting reflex" at opportune times. There is also (iii) a third user impact module, being a psychotherapy treatment module, to receive input from a user, recognize symptoms of a mental illness, define a treatment regimen, and provide corrective guidance and treatment to a user. While basic treatment methods are employed, adjustments in level of treatment, frequency of treatment and even choices of appropriate treatment evolve through initial analysis followed by artificial intelligence fine tuning. This fine tuning is in the form of AI iterative adjustments, or shifting to different methodologies, as needed, or both. There is further (iv) a fourth user impact module, being a biofeedback module to receive user bio-information and to record and direct biofeedback data. By "biofeedback" is meant medical information and psychological information for storage and for third party overseer review and action, as necessary. The medical data may be processed within the CPU or forwarded to a cloud system or host for processing and delivery for review by practitioners. There is also (v) a fifth user impact module, being an emergency high risk alert system to receive and recognize high risk or suicidal tendencies and to report them as an emergency to a third-party monitor, such as a practitioner or emergency response center. Different high risk feedback may require different responses. Some patients who become suicidal may need increased or changed or new antidepressant medication, while others may need personal care, such as in an institution or clinic, or hospital. Threats to third parties, such as, "I want to kill my neighbor", may require intense treatment beyond robotic treatment. The critical aspect here is that the robot will recognize high risk statements, actions and reactions of the user and report them for external follow-up. There is also (vi) a pressure sensing-responding software connected to exoskin sensors and to provide positive feedback to a user in response to sensing of inward pressure. Such responses may be a robotic smile, a wink, an encouraging spoken message or combinations of these. There is also (vii) camera receiving software with emotional identification features. Thus, the camera(s) with the facial recognition software and the AI, provides data for comparison to various recognized stored facial expressions and concludes certain emotions and to select appropriate responses, when deemed necessary. Again, the AI will evolve iteratively refined recognitions and responses. There is further (viii) emotional expressions software to provide a user with selected emotional responses via at least one emotional expression mechanism selected from the group consisting of movement of the robot head, movement of a component of the head, light changes, audio outputs, and artificial intelligence speech outputs, as well as other software and hardware consistent with the foregoing.

Figure 2:
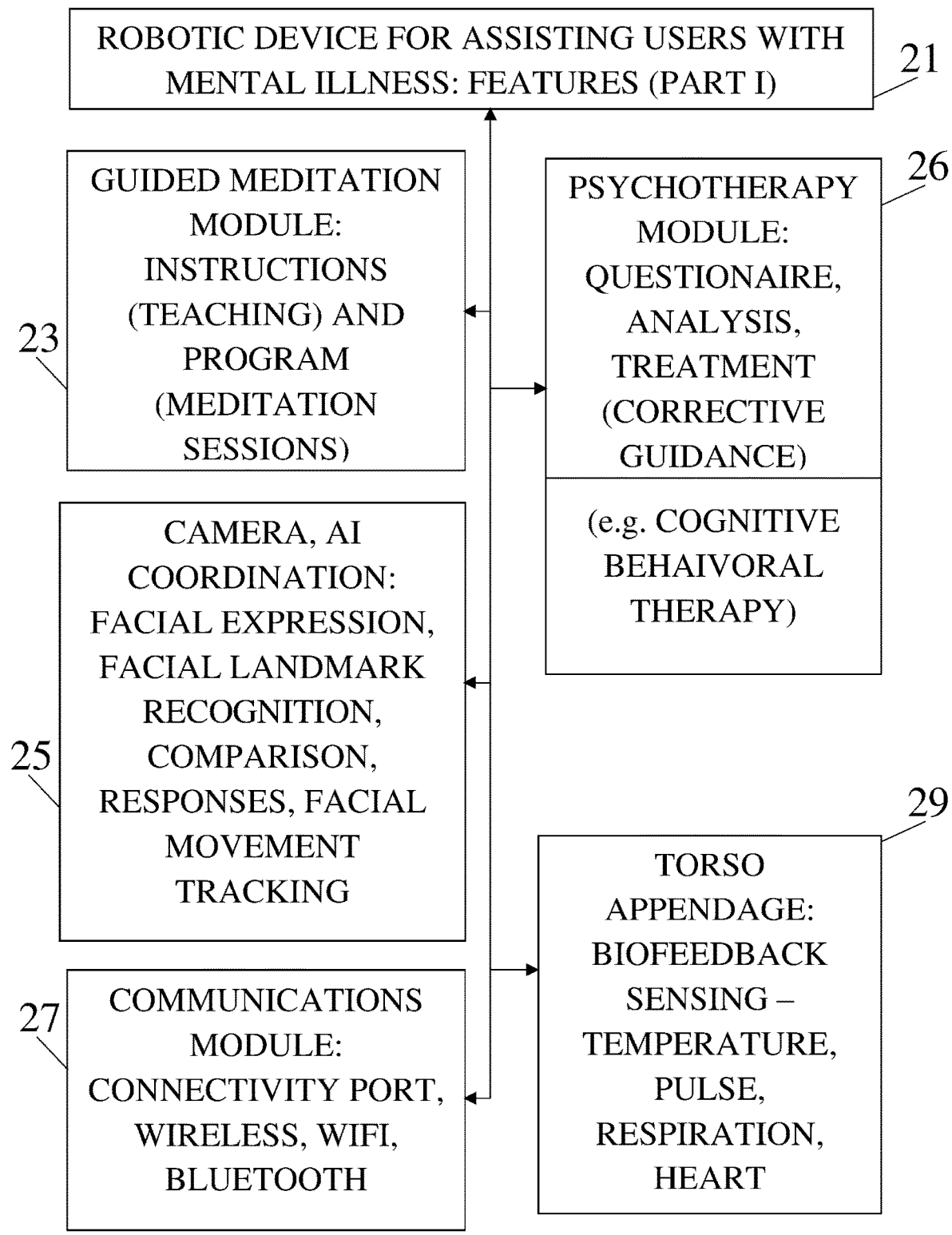
FIG. 2 shows a block diagram of some specific aspects of a present invention robotic device.

FIG. 2 block diagram illustrates some more of the details of some of the present invention features, frame 21, discussed above. Frame 23 shows preferred guided meditation module that includes both teaching instructions, so that a user can learn meditation techniques and then utilize them without robotic assistance, as well as programmed meditation sessions. This latter feature enables users to set up a meditation session schedule or just have random sessions as desired, with the robot. Frame 25 illustrates the use of cameras and AI coordination to analyze and create facial expressions through facial landmark recognition, comparison, and responses. Facial movement tracking is a part of this feature. It is also preferred to have the head and/or eyes of the robot move to at least partially follow movement of a user. Frame 26 references some embodiments of the psychotherapy module with corrective guidance for the user, and indicates cognitive behavioral therapy, which is a preferred embodiment. Frame 29 indicates that a torso appendage may be included and this appendage would incorporate biofeedback sensors—such as pulse, body temperature, respiration rate, heart rates (blood pressure).

Figure 3:
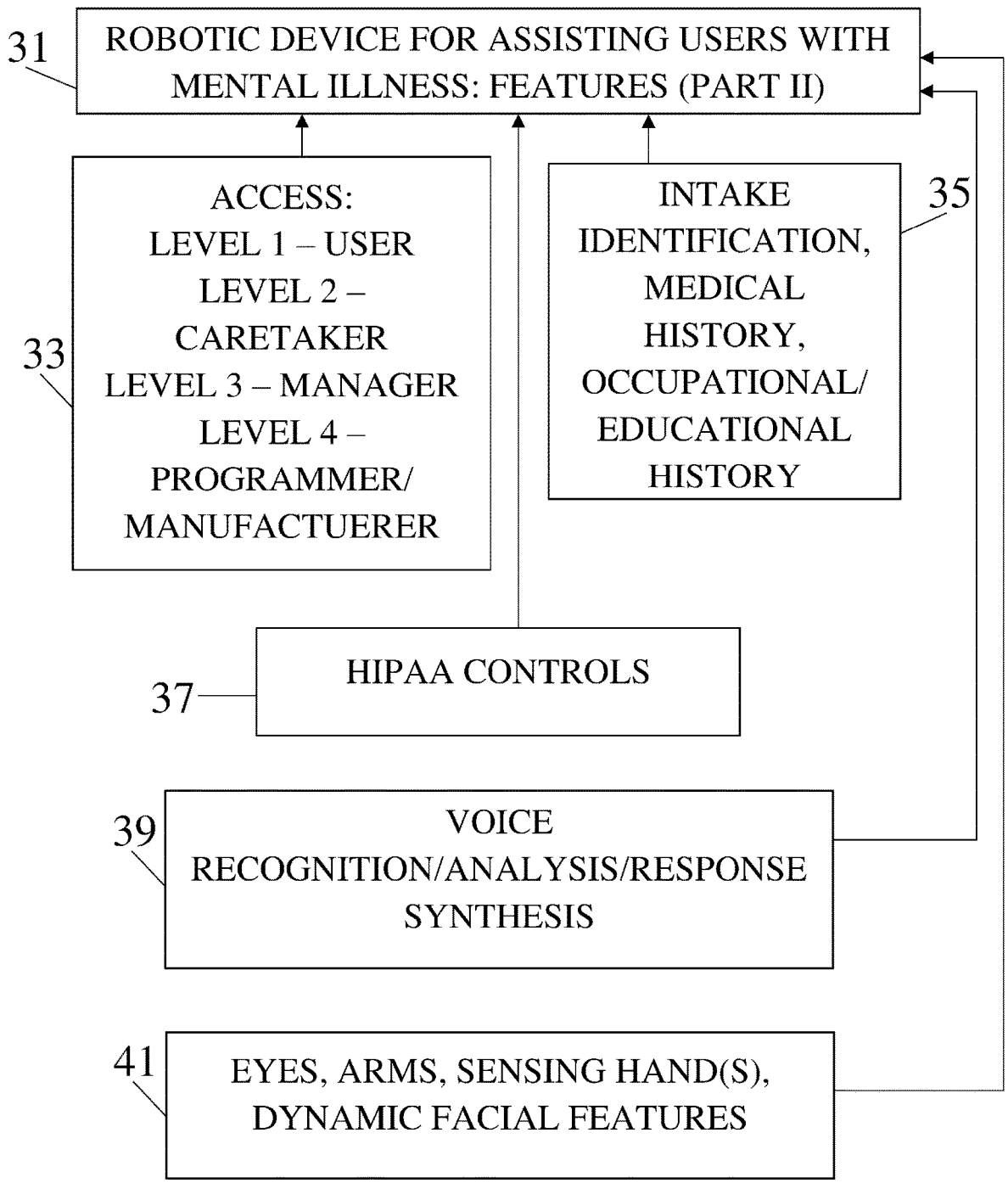
FIG. 3 shows another block diagram of some specific aspects of a present invention robotic device, including levels of security/access.

FIG. 3 block diagram illustrates more of the details of some other present invention features, frame 31. Frame 33 shows possible security features of the present invention robotic device. Three access levels are beneficial and four are preferred. They are Level 1—User Access; Level 2—Caretaker Access; Level 3—Manager Access; and Level 4-programmer/Manufacturer Access. Level 1 provides the lowest (least) access and Level 4 provides the highest level. Thus, a user can log in or activate just by voice command, by could not adjust or delete programs or reschedule or move or alter data. The caretaker can make some adjustments to schedules and other choices. The manager could access all data, medical history, and change treatments, close out or initiate old/new caretakers, etc. The programmer/manufacturer would be able to perform corrective actions, such as upgrade programs. Frame 35 calls for ID intake and other personal/medical data of a user. This could be a prerequisite to initializing the robot for providing user services. Frame 37 suggests HIPAA controls as a mechanism to allow a user's designee to access the user's medical and other records associated with or connected to the present invention robotic device. Thus, a user can permit third parties to access certain data by interacting (talking or using the touchscreen or touchpad), to authorize release and transmittal of his/her medical data. Frame 39 emphasizes voice recognition/analysis/response synthesis, and frame 41 shows one example of a present invention robot with eyes, arms, sensing hands and dynamic features. Sensing hands can be held by a user to evoke a friendly or encouraging robotic gesture and/or spoken response, as well as sensors such as pulse and temperature sensors strategically positioned in the robot's hand.

Figure 4:
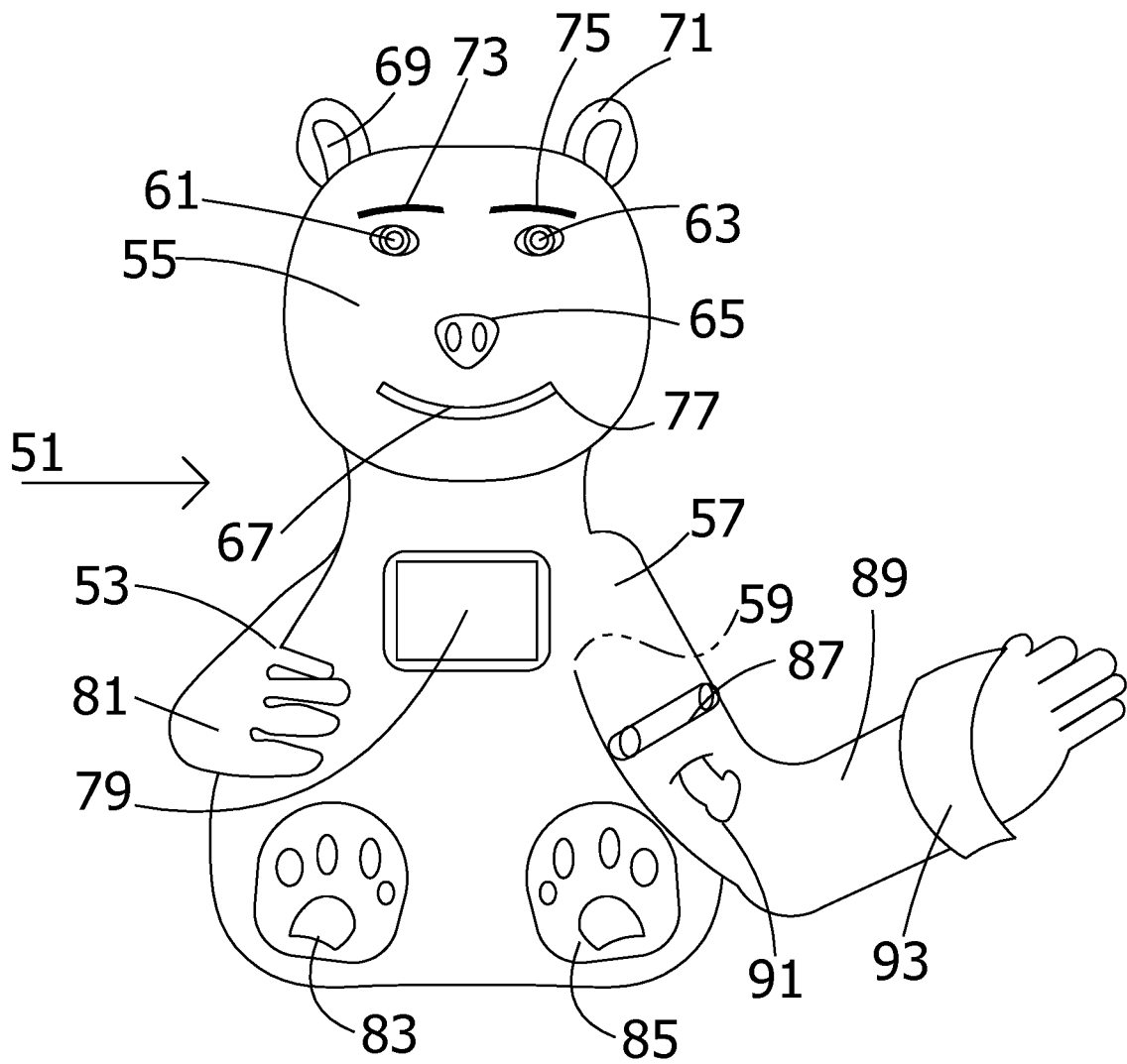
FIG. 4 shows a front view of an embodiment of a present invention robotic device, in the form of a sitting polar bear.

FIG. 4 shows a front view of an embodiment of a present invention robotic device, in this case a sitting polar bear 51. This polar bear 51 includes a torso 57 with a head 55 and appendages such as arm 53 and arm 89, with short or no legs and with feet 83 and 85. There are significant internal aspects (not shown, but described in previous paragraphs) that would include the support frame, the CPU, the power source, the wiring, cameras, microphones, speakers, etc., and the hardware and software previously described above. The head 55 includes moveable eyebrows 73 and 75 and microphones in ears 69 and 71, a moveable mouth 77 with a speaker 67 inside, and bear nose 65. Eyes 61 and 63 contain cameras and may shift left/right/up/down. There is a squeezable hand 81 on arm 53 that causes the robot to favorably respond to a squeeze. Likewise, body portion 59 has a cuddly soft exoskin with hidden sensors, that recognize a body hug and the robot responds favorably. On the opposite arm 89, which is extended for functional purposes, is set up so that a user may insert an arm into blood pressure loop 93 and move the hand (fist) down to grip handle 87 ending with the upper arm in blood pressure loop 93, and wrist on pulse pad 91. These mechanisms assist in collecting medical data as well as assist in identifying high risk situations such as acutely elevated blood pressure, or fever. Taken with camera and speech data, they can also support conclusions of extreme stress, depression or severe health issues.

Figure 5:
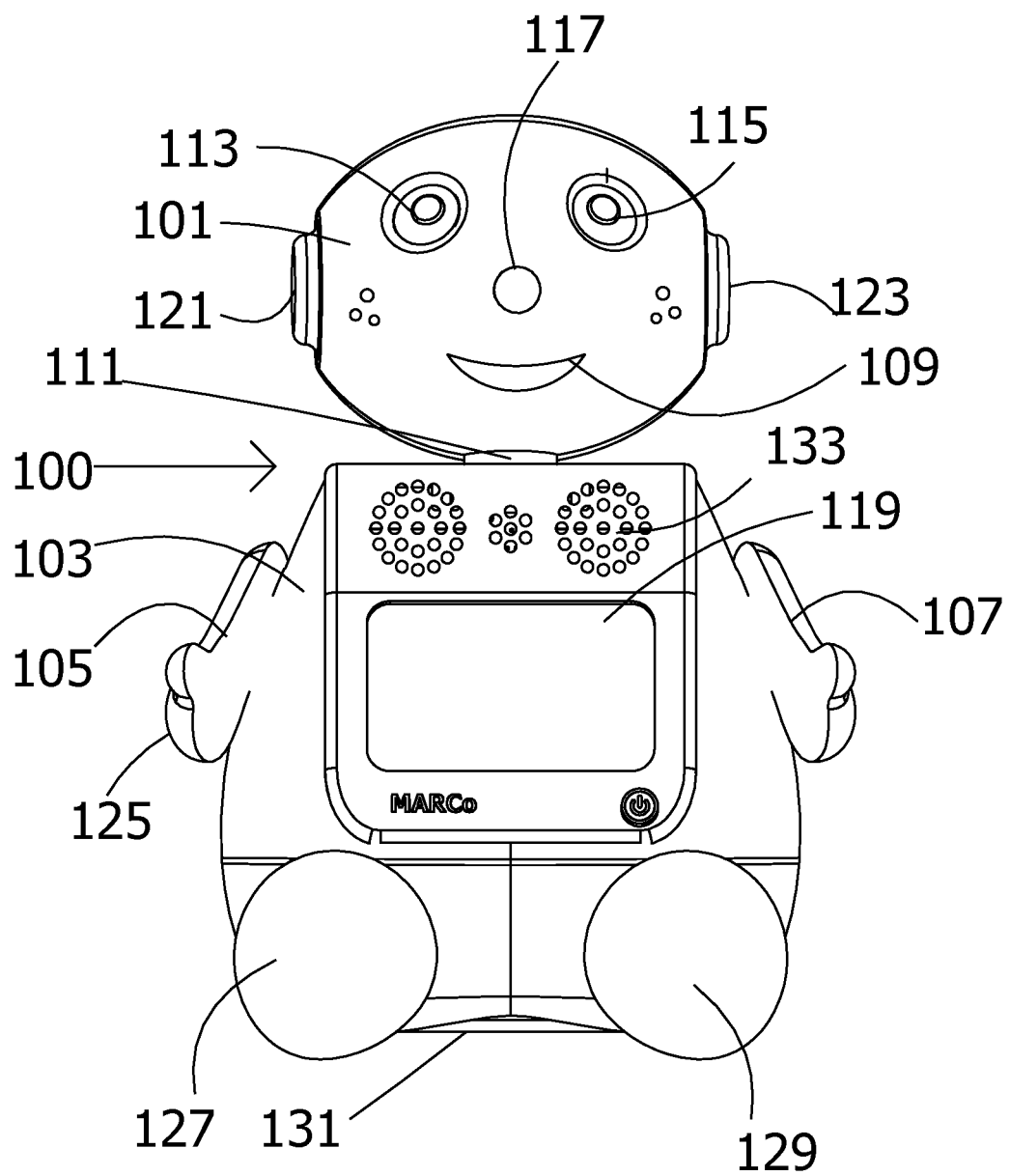
FIG. 5 shows a front oblique view of an embodiment of a present invention robotic device, with humanoid features.
Figure 6:
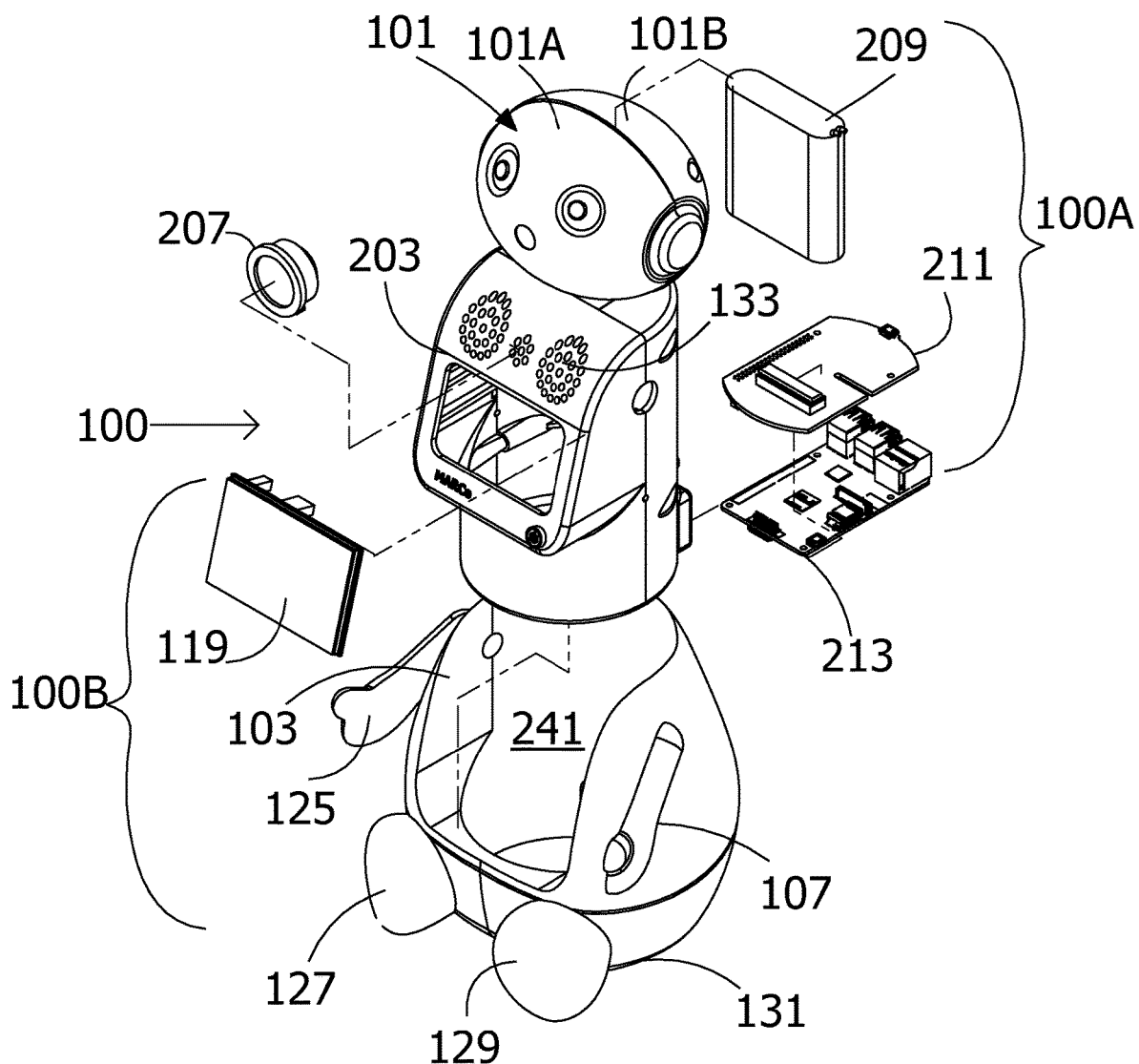
FIG. 6 shows a front oblique, exploded view of the embodiment of a present invention robotic device shown in FIG. 5.

FIG. 5 depicts another embodiment of the present invention robotic device in a front view perspective. As shown in this view, the invention robot 100 is embodied in a humanoid form with appendages, meant to generally mimic a happy human-like figure. Thus, robot 100 includes a head 101 and a torso 103, as well as arms 105 and 107, legs 127 and 129, eyes 113 and 115 that contain tracking cameras, a nose 117, a mouth 109 with a microphone for receiving user speech inputs, ears 121 and 123, a head-supporting, head-rotating neck 111, and other facial features and facial functions. In this embodiment, the support frame is comprised of two distinct components supporting two different subassemblies, referred to as the upper body 100A and the lower body 100B, are described in conjunction with the exploded view of FIG. 6 below. Here, the lower body 111 at torso 103 is the shell of the body that includes the exoskin that is made of soft cell foam that is either cast or produced via subtractive manufacturing methods or otherwise. The purpose of this is to provide a squeezable stress relief, huggable body similar to a large stress ball to assist in calming a patient. This outer shell may or may not have an external cloth covering the foam body for aesthetic purposes or to suit a particular user's desires. The exoskin contains pressure sensors in order to detect when the foam is being squeezed. These sensors are connected to an internal CPU and alert the system when the unit is being squeezed to detect the need for an affectionate or supportive retort and/or to help identify elevated stress levels in the user. An optical pulse sensor is embedded inside the hand of the body, as indicated by hand 125, to read a user's pulse and monitor to receive and record data and to identify deviations from average heartrate readings. A touch pad or touch-screen 119 is positioned in the center of the body, as shown, to provide a main interface for the user. It functions as a keyboard, and as a screen for any other computer or TV screen purposes. The invention's main application's Graphical User interface (GUI) is displayed on this screen. It deploys visual treatment methods such as videos employed in guided meditation techniques and images and text for cheering its companion up based on a user's personal preferences and personality. External applications can be run through this touch screen as well to assist in psychiatric evaluation as desired by the owner of the unit. Above the touch screen 119, is an additional dual speaker unit, see speaker 133. These speakers are embedded inside the upper body 100A (FIG. 6). These speakers, with related connections and CPU AI and other software, allow for the invention to synthesize human speech for conversation and play audio files such as, but not limited to, soothing music and noise for guided meditation or for engaging a user. One option for this embodiment would be to have another speaker in mouth 109 for the robot to speak, and to use the others for other purposes, such as sound with videos, music, etc. The lower body 100B (FIG. 6) has a bottom 131 that is mostly flat so as to provide a stable resting base to support robot 100 in the sitting position shown in FIG. 5.

Also in FIG. 5, the head 101 assembly is comprised of a plastic or other structural encasement taking the form of a humanoid head. The preferred plastic used here may be an impact resistant plastic such as ABS or polycarbonate to improve the invention's ability to withstand being dropped, thrown, or hit. The head 101 contains an audio and visual package combining imaging cameras in eyes 113 and 115, and a microphone in mouth 101. The cameras, with related connections and CPU AI and other software, allow for facial recognition, object recognition, individual recognition, emotion recognition, and image and video recording for the purposes of establishing and retaining a history, providing that history for AI evolution and for caretakers and others to review and make possible adjustments, and, for thereby improving treatment. The microphone in mouth 101 allows the invention to listen to a user's speech and convert it into text for the main application to break down, analyze and to generate a proper response. The head 101 also contains an array of RGBW LED lights in each eye socket which can change color and luminous intensity in order to match a user's mood, present an alternative, more favorable mood, and treat illnesses such as seasonal affective disorder, provide visual stimulus for treatment, and general user interaction. The head 101 is motorized with two degrees of freedom such that the head can pan about an axis that runs from the base of the unit to the top of the head 101, and tilt around an axis parallel to the ground through the midsection of the head 101 when viewed from the front. These motions are limited mechanically such that the displacement of the head 101 from its no' mal position, as defined by this drawing, may not exceed specified maximum and minimum positions. As mentioned, neck 111 is a part of the motion component and, in one embodiment, is like a universal joint to head 101 with predetermined movement limits, controlled by the feedback to and from the CPU.

Figure 7:
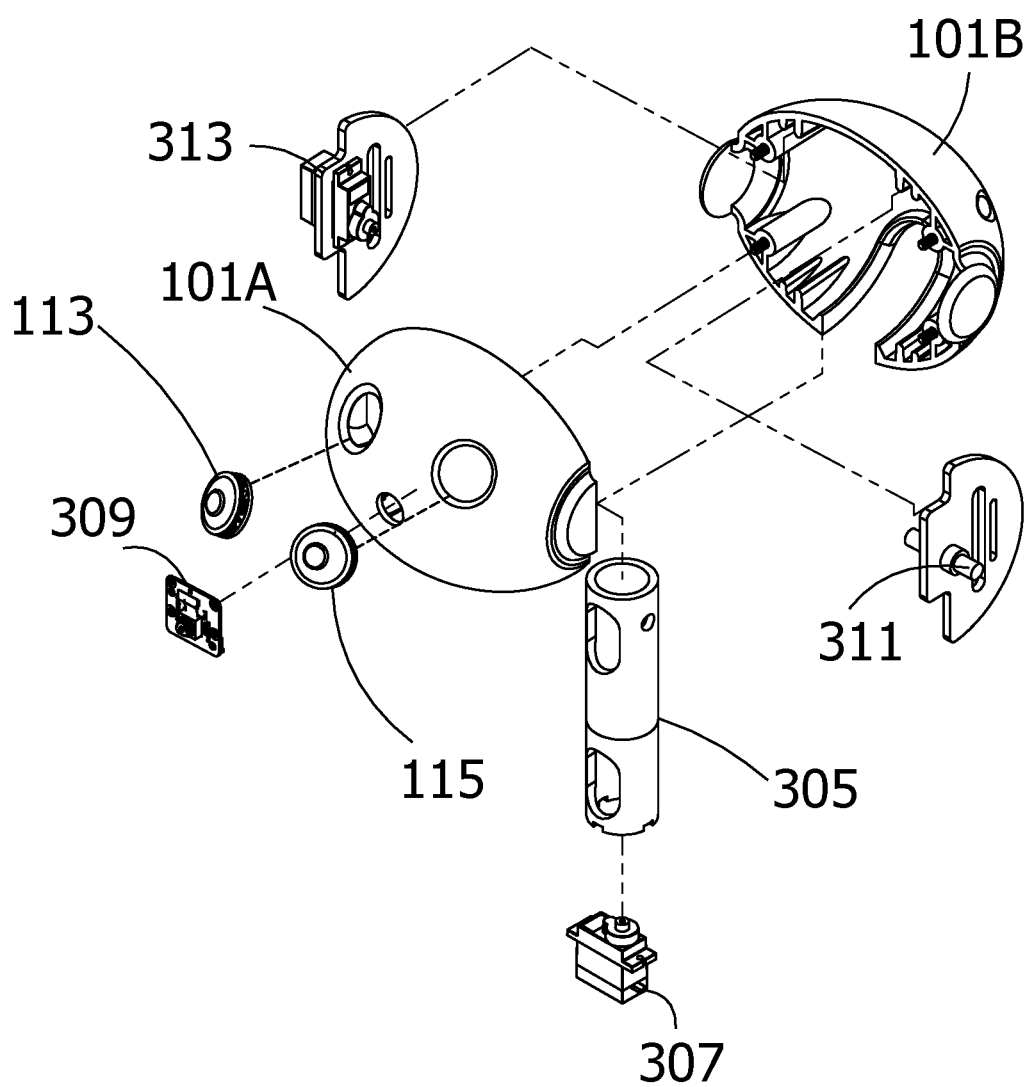
FIG. 7 shows a front oblique, exploded view of the head of the present invention robotic device shown in FIGS. 5 and 6.

FIG. 6 displays an exploded view of the invention's robot 100 with its upper body 100A and its lower body 100B. These are two subassemblies that is displayed as a complete unit, as consistent with this embodiment. The lower body 100B includes the exoskin pressure-sensitive foam body encasement and is designed to receive and lock in upper body 100A. Thus, a person with the correct key or code may unlock and lift upper body 100A from lower body 100B nesting receptacle 241, and service, modify or repair upper body 100A components and then return upper body 100A to its nesting receptacle 241 and lock it in by key or code. Note that in FIG. 6, some identical parts shown in FIG. 5 are identically numbered and need not be re-described here. In addition, head 101 is shown to have separable head front 101A and head rear 1019. This is elaborated upon in FIG. 7 below. In this embodiment, all of the functional "guts" are contained within the upper body 100A, except for sensors in the lower body 101B (the pressure sensors and medical data sensors that are plug-in or otherwise connected to the upper body 100A components (CPU, software, etc.). Thus, upper body 100A includes the head 101 and its functional aspects and details described above and below, as well as speaker 207, battery pack 209, coprocessor hub 211 and central processing unit computer 213. The two-component main support frame here (support internal for upper body 100A and lower body 100B) is comprised of a structurally appropriate material or group of materials, such as plastic, metal (lightweight aluminum is preferred), carbon fiber, composites and combinations of these. The neck (shown in detail in FIG. 7 area which joins to the head 101, with a midsection containing the CPU, hardware and software described above. This two-component main support frame provides the support for robot 100 and also contains mounting holes, brackets, and other similar features for the internal and external electronics. The single-board computer 213 is mounted into the back of the upper body 1001, and is connected to hub 211. This single board computer contains the CPU that runs the operating system and the main software and applications of the robot 100. The computer has a built-in network card and WIFI antenna to allow the device to connect to remote networks. As mentioned, peripheral hardware including the touch screen, cameras, microphone, and speakers connect directly to the main processor and are accessed directly by the software, while sensors and motors are controlled and monitored via a secondary processor, which is connected to the main processor as either a co-processor on a single board or a separate controller with a serial connection. The single board computer 213 contains ports for network, serial, audio, and visual connectivity, as well as a storage device for additional memory. Separate hub 211, is introduced in the unit to allow for additional serial and network ports for expanding the number of connections that can be made to the main board, adding additional peripheral hardware, and allowing external users to connect to the internal processor. This hub 211 will also allow the single board computer to connect to a network over a cable rather than over WIFI if wireless connectivity is not achievable. The unit is powered by a battery pack 209, which allows the unit to work while either plugged into a wall outlet, connected to a USB based power source, or disconnected from any external power sources.

FIG. 7 depicts an exploded view of the head 101 subassembly, with head front 101A and head rear 101B separated, but fastened together by connecting gusset plates 313 and 311. The cameras are located in eyes 113 and 115, and are connected to the CPU as described above. Microphone audio input package 309 and optional output speaker is placed behind nose 117 and mouth 109 (FIG. 5). The cameras and microphone encasement are connected to the CPU in this embodiment via a position-based tilt servo motor 307 in neck 305 and inputs are processed and used to interact with servo motor 307, for example, to follow the movement of a user and/or to show motion as part of a response or dialogue. This motor allows head 101 to rotate to a maximum of forty-five degrees up or down when facing the viewer. A second position-based servo motor inside neck 305, is connected on its stationary base to the neck joint of the invention, via mechanical connection. In this embodiment, the output axle of the motor is connected to the base of the head 101. The positioning of this motor allows for forty-five degrees left or right when viewed straight forward by the user. Mounting hardware including bolts, pins, and bearings, as indicated by 308, are used to connect the two halves of the head encasement. Two identical arrays of RGBW LEDs are installed inside the eye sockets of eye 113 and 115.

Figure 8:
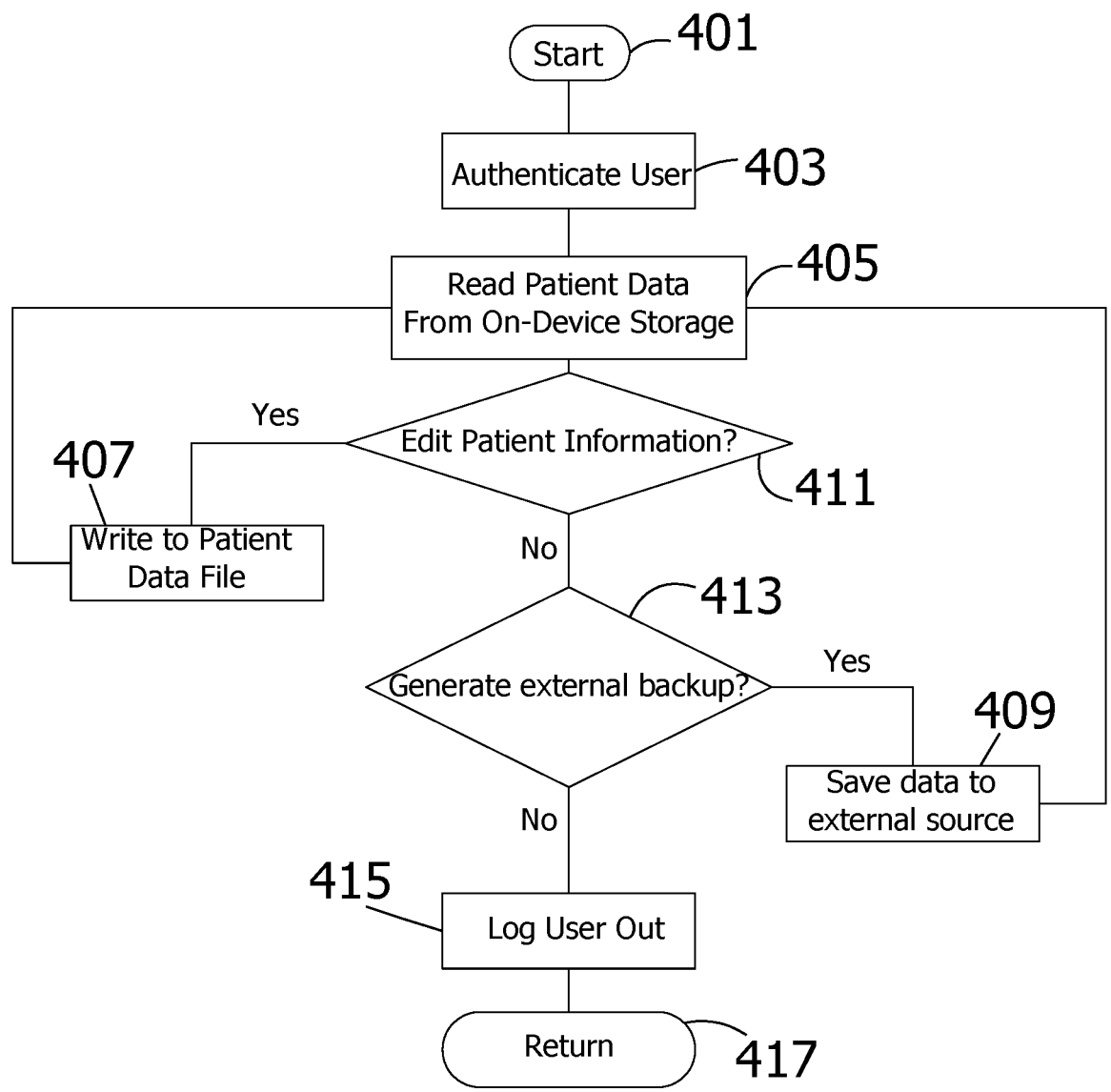
FIG. 8 shows a diagram of one aspect of software functionality of an embodiment of the top view of an embodiment of a present invention robot; and, FIG. 9 shows a diagram of one aspect of software functionality of another embodiment of the top view of an embodiment of a present invention robot.

FIG. 8 depicts a software diagram for the invention's main application. This application handles all major functionality of the invention. The application performs its tasks on a per-user basis, so in order to deliver its treatment, it identifies a user at the start of its session. The present identification process of this embodiment may be that described in FIG. 3 above. Once the user is captured by the cameras after an initial use, this embodiment uses a combination of facial recognition and voice/name recognition in order to determine the identity of the user. The start 401 may be audibly of otherwise physically initiated. Next, the user must be authenticated 403. The patient data on storage is read 405 for comparison to the new data from the user at hand. If there is a match, the user is "in". If a user is not identified by either his or her facial features or by voice/name, the user may be added as user to its list of known users and patient information is edited 411 and written into the patient data file 407. It will prompt the user for their full name and preferred name, and record images of his or her face to serve as training data for the software's facial recognition algorithms. There is a general backup that is external 413, wherein the new data is also saved to the external source 409. If the user is accepted then the robotic support is initiated. Log out 415 is performed, such as verbally, on the touch screen or by time out (preset time, such as 10 minutes without activity, action or voice from the user), with a safety lock that initiates if a different voice (not the user) tries to use the system. Return 417 is available in the event of a log out or time out and the user wishes to continue.

Figure 9:
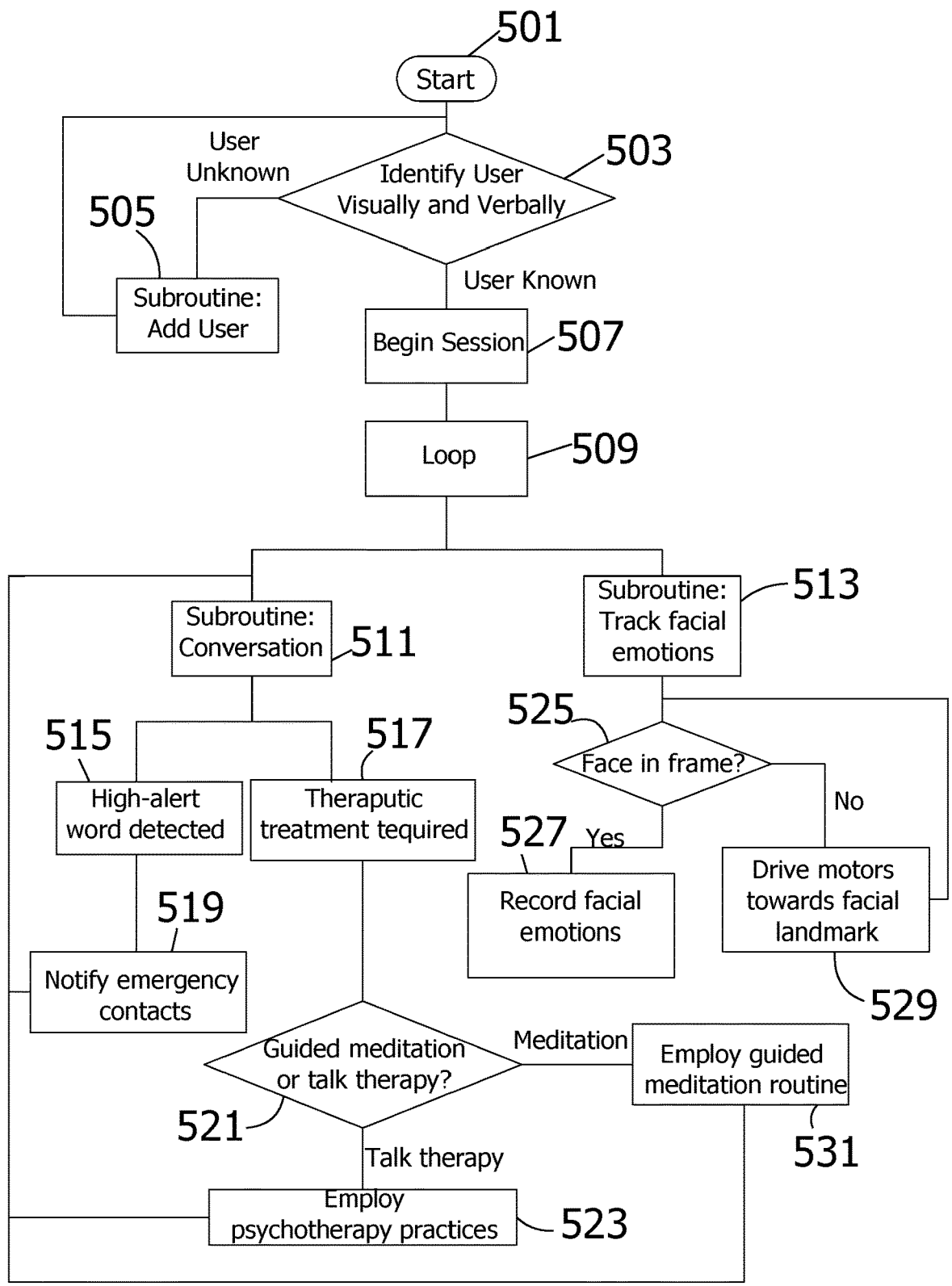

FIG. 9 illustrates another software diagram (basic architecture) wherein the start 501 is accomplished by a user speaking and then followed by the patient being authenticated visually and verbally 503. The patient data from the robot storage is read 405 and compared. If the user (patient) is not recognized, then editing the patient information through an add user subroutine 505 is initiated 411 is initiated, written to file and backup as in FIG. 8 above, and saved to external source. Once a user is added or identified (authenticated), the application may begin a new treatment session 507 via loop 509 for analysis and selection of robotic action. Each treatment session uses speech recognition to break down a user's speech and generate a proper response with the use of synthesized speech abilities. In this embodiment, the conversation algorithms 511 and facial tracking and facial emotions 513 are accessed remotely from a network based artificially intelligent speech and facial landmark recognition algorithms. These algorithms are capable of breaking down a user's speech to identify key phrases or words, or provide small talk and general responses if none are detected. These key phrases and words can be trained to provide a broad range of conversational routes and directions. They are also used to identify facial landmarks by comparing user's landmarks to stored landmarks to develop operative conclusions with a correspondingly appropriate response or set of responses. Different forms of treatment can be triggered by key phrases and/or combinations of facial landmarks, as well. Once the user's face is in frame 525 the user's facial emotions are recorded 527; if the user's face is not in frame then drive motors 529 correct through head movement to place the user's face in proper frame. The present invention robot in this embodiment, using conversation 511, can recognize high alert words, word combinations, phrases and sentences, and act accordingly. For example, if a user says "Things aren't going well. I feel like hanging myself" or "I can't wait to see the Doctor, I'm going to double the prescription on my own" or key words, such as "suicide", "kill" "punch", these are recognized as high alert phrases or words that will initiate notification by the robot to emergency contacts 519, for professional handling. This may also trigger psychotherapy practices 523 and/or meditation routines 531. If through conversation 511, the system sees the need for therapeutic treatment 517, a choice of guided meditation or talk therapy or both 521 may be offered or recommended, and psychotherapy practices 523 and/or meditation routine 531 will begin.

As would be a feature in the FIG. 9 embodiment, so too will the following apply to other embodiments of this invention. Thus, in addition to the robot's analysis leading the process, the patient may make requests that, if deemed reasonable by the AI, will be granted. For example, if a user requests meditation verbally, the application will select a guided meditation routine using a combination of prerecorded videos, music, and sounds to help soothe the user. This can also be actuated routinely if a user verbally sets a recurring time he or she would like to meditate, or if a caregiver provides the unit with the same command. If a user's speech contains information about themselves, the unit can train itself and update the user's profile to match the new or additional data. If the user relays information that either contains data about their mental or physical health that implies a negative trend, or if the words and phrasing used match the pattern of distorted thinking, as specified from generally accepted psychological treatment, the unit will deploy talk therapy, formally known as cognitive behavioral treatment (CBT). This treatment includes a purely verbal exchange to identify the roots of a patient's current mental or physical state, and offering potential solutions of how to help the user cope. If the user speaks a phrase that contains high alert words, which include but are not limited to, suicide, self-harm, or harm of others, the invention will connect to a network-based service for sending out messages to emergency contacts of the patient. It will verbally garner additional information of a patient's status based on generally accepted psychological practices including but not limited to the Columbia Suicide Severity Rating Scale, and send a complete report of this information to the patient's specified emergency contact information. In this embodiment, the information is sent over an SMS text message. The main software additional deploys visual emotion recognition for identifying a user's facial emotions. Facial landmarks are identified and compared to training data to determine a user's probable emotion or combinations of emotions. To keep the user's face in the video frame, the facial landmarks are also used to drive the positioning motors of the head. If the user's head drifts too far to anyone edge of the video frame, the application will give a drive command to the two head motors to adjust its position to re-center the head in the frame. The general trend of the user's facial emotions over time can be recorded and tracked in conjunction with the other forms of treatment deployed to determine how a treatment affected the user's overall emotional and mental wellness. FIG. 9 therefore also depicts a software diagram for the invention's secondary application. This application is accessed by connecting an external computer to the unit over a cable connection. It allows an authorized user or emergency personnel member to audit patient data, modify unit information, and generate external backups of patient information. The software uses a username and password authentication process to verify that the user is verified. It accesses the same patient data that the main application accesses, which in this embodiment is stored in a JSON format, and converts it to readable text by specific or desired fields. The authorized user is allowed an option to add or modify patient information or unit information, which the application then writes to the patient data. If the user selects to generate an external backup, the requested data will be transferred to the connected external computer to a directory of the user's choice. Once all procedures are finished, the user is logged out and the secondary computer is disconnected.

Although particular embodiments of the invention have been described in detail herein with reference to the accompanying drawings, it is to be understood that the invention is not limited to those particular embodiments, and that various changes and modifications may be affected therein by one skilled in the art without departing from the scope or spirit of the invention as defined in the appended claims. For example, the actual shape of the robot may be any of numerous possibilities as long as its functionality as described is not affected adversely. Also, as another example, the software could include entertainment, games, intellectual challenges and mind-building subprograms.

What is claimed is:

1. A robotic device for assisting users with a mental illness, which comprises:
    (a) a robotic support frame having sufficient structure to support the subsequently described components, and having a main torso and a head;
    (b) a central processing unit within said robotic support frame, said central processing unit including software to operate at least five user impact modules and including artificial intelligence software, voice recognition software, speech output software, and a graphical user interface connected to an external screen;
    (c) a power supply component selected from the group consisting of internal power supply and external power connection, connected to said central processing unit;
    (d) said external screen attached to said robotic support frame and having visual display output and having at least touch screen input;
    (e) at least one camera attached to said robotic support frame for viewing a user and connected to said central processing unit;
    (f) at least one microphone attached to said robotic support frame for receiving audio input and connected to said central processing unit;
    (g) at least one speaker attached to said robotic support frame for transmitting audio output and connected to said central processing unit;
    (h) hardware and additional software functionally connected to said central processing unit and to said artificial intelligence software, to said voice recognition software, and to said speech output software, and at least five user impact modules including:
  (i) a first user impact module, being a companion module, with two-way communications to establish companionship with a user;
  (ii) a second user impact module, being a guided meditation module, to provide assistance to a user in conducting personal meditation;
  (iii) a third user impact module, being a psychotherapy treatment module, to receive input from a user, recognize symptoms of a mental illness, define a treatment regimen, and provide corrective guidance and treatment to a user;
  (iv) a fourth user impact module, being a biofeedback module to receive user bio-information and to record and direct biofeedback data;
  (v) a fifth user impact module, being an emergency high risk alert system to receive and recognize suicidal tendencies and to report said suicidal tendencies as an emergency to a third party monitor;
  (vi) a pressure sensing-responding software connected to exoskin sensors and providing positive feedback to a user in response to sensing of inward pressure;
  (vii) camera receiving software with emotional identification features;
  (viii) emotional expressions software to provide a user with selected emotional responses via at least one emotional expression mechanism selected from the group consisting of movement of said head, movement of a component of said head, light changes, audio outputs, and artificial intelligence speech outputs;
(i) an exoskin attached to at least a portion of said robotic support frame, said exoskin having a plurality of sensors for sensing inward pressure, said plurality of sensors being connected to said pressure sensing-responding software of said central processing unit; and
(j) at least three distinct levels of entry security for access to said central processing unit, including:
  (i) a first level of security, being a user's level of security, permitting a user to be recognized and to be limited in the use of said robotic device only for user designated purposes and to exclude a user from altering, transferring and eliminating data, from entering a higher level of security, thereby being prevented from operating at said levels of security;
  (ii) a second level of security, being a caretaker level of security, and being a higher level of security than said first level of security, and permitting access to said first level of security, and permitting access to user data for review and report functions, permitting user programming for interaction with various portions of each of said at least five user impact modules;
  (iii) a third level of security, being a manager level of security, and being a higher level of security than said first level of security and said second level of security, and permitting access to said first level of security and said second level of security, and at least permitting access to software for modification and for replacement, for reviewing interaction between a user and a caretaker, and for modifying a treatment for a user.

2. The robotic device for assisting users with a mental illness of claim 1 wherein said guided meditation module includes pre-meditation training sessions and actual meditation sessions guiding a user through meditation.

3. The robotic device for assisting users with a mental illness of claim 1 wherein said mental illness treatment module includes diagnosis analysis with appropriate questions to a user and storage and analysis of responses from a user, and subsequent instructional sessions providing a user with alternative reactions to negative emotion situations.

4. The robotic device for assisting users with a mental illness of claim 3 wherein said mental illness treatment module includes use of recognized behavioral therapy.

5. The robotic device for assisting users with a mental illness of claim 4 wherein said recognized behavior therapy is cognitive behavioral therapy.

6. The robotic device for assisting users with a mental illness of claim 1 wherein said exoskin is attached to said torso to enable a user hugging feature that initiates a positive response from said robotic device.

7. The robotic device for assisting users with a mental illness of claim 1 wherein said artificial intelligence software includes visual emotion recognition that studies a user's facial expression, identifies facial landmarks, compares said facial landmarks to training data, determines the user's emotional state and responds with a defined response to said emotional state.

8. The robotic device for assisting users with a mental illness of claim 7 wherein said software includes facial movement tracking and hardware connected to said camera to move said camera in response to positional movement of said facial landmarks of said user.

9. The robotic device for assisting users with a mental illness of claim 1 which further includes a communications module for external connectivity that includes at least one communications unit selected from the group consisting of a connectivity port and wireless transmitter-receiver and WIFI connectivity.

10. The robotic device for assisting users with a mental illness of claim 1 wherein said robotic device further includes at an appendage with a human physical data sensing mechanism with user contact sensing of at least one parameter selected from the group consisting of pulse, temperature, and aspiration rate.

11. The robotic device for assisting users with a mental illness of claim 1 wherein said robotic device further includes a fourth level of security, being a manufacturer's level of security, and permitting access to said first level of security, said second level of security, and said third level of security and permitting hardware and software modifications, replacements and bypasses.

12. The robotic device for assisting users with a mental illness of claim 1 wherein said mental illness treatment module includes diagnosis analysis with appropriate questions to a user and storage and analysis of responses from a user, and subsequent instructional sessions providing a user with alternative reactions to negative emotion situations.

13. The robotic device for assisting users with a mental illness of claim 12 wherein said mental illness treatment module includes use of recognized behavioral therapy.

14. The robotic device for assisting users with a mental illness of claim 13 wherein said recognized behavior therapy is cognitive behavioral therapy.

15. The robotic device for assisting users with a mental illness of claim 1 wherein said foam exoskin is attached to said torso to enable a user hugging feature that initiates a positive response from said robotic device.

16. The robotic device for assisting users with a mental illness of claim 1 wherein said artificial intelligence software includes visual emotion recognition that studies a user's facial expression, identifies facial landmarks, compares said facial landmarks to training data, determines the user's emotional state and responds with a defined response to said emotional state.

17. The robotic device for assisting users with a mental illness of claim 16 wherein said software includes facial movement tracking and hardware connected to said camera to move said camera in response to positional movement of said facial landmarks of said user.

18. The robotic device for assisting users with a mental illness of claim 1 which further includes a communications module for external connectivity that includes at least one communications unit selected from the group consisting of a connectivity port and wireless transmitter-receiver and WIFI connectivity.

19. The robotic device for assisting users with a mental illness of claim 1 wherein said robotic device further includes at an appendage with a human physical data sensing mechanism with user contact sensing of at least one parameter selected from the group consisting of pulse, temperature, and aspiration rate.

* * * * *